United States Patent
Plewright et al.

(10) Patent No.: US 9,072,801 B2
(45) Date of Patent: Jul. 7, 2015

(54) STERILISER UNIT

(75) Inventors: Glen Plewright, Bullcreek (AU); Michael Dixon, East Perth (AU)

(73) Assignee: STAFFARENA CORPORATION PTY LTD, Bullcreek (AU)

( * ) Notice: Subject to any disclaimer, the term of this patent is extended or adjusted under 35 U.S.C. 154(b) by 1129 days.

(21) Appl. No.: 13/055,097

(22) PCT Filed: Jul. 20, 2009

(86) PCT No.: PCT/AU2009/000922
§ 371 (c)(1),
(2), (4) Date: May 24, 2011

(87) PCT Pub. No.: WO2010/009497
PCT Pub. Date: Jan. 28, 2010

(65) Prior Publication Data
US 2011/0225753 A1    Sep. 22, 2011

(30) Foreign Application Priority Data
Jul. 23, 2008    (AU) ................................ 2008203290

(51) Int. Cl.
*A61L 2/00* (2006.01)
*A61L 2/18* (2006.01)
*A61L 2/26* (2006.01)

(52) U.S. Cl.
CPC ... *A61L 2/18* (2013.01); *A61L 2/26* (2013.01); *A61L 2202/15* (2013.01)

(58) Field of Classification Search
CPC .......... A61L 2/18; A61L 2/26; A61L 2202/15
USPC ................................. 422/301, 294
See application file for complete search history.

(56) References Cited

U.S. PATENT DOCUMENTS 2,664,584 A    1/1954    Twerdahl et al.
6,270,275 B1    8/2001    Martz
(Continued)

FOREIGN PATENT DOCUMENTS

WO    WO2007039120 A1    4/2007

OTHER PUBLICATIONS

Extended European Search Report reference 8005/P/1001-WO Application No. 09799855.3-2113/2326354 PCT/AU2009000922.
(Continued)

*Primary Examiner* — Kevin Joyner
(74) *Attorney, Agent, or Firm* — Andrews Kurth LLP; Sean S. Wooden

(57) ABSTRACT

The invention concerns a sterilizer unit (10) for sterilizing an absorbent body (30), such as a sponge. The sterilizer unit firstly comprises a container (12) for holding a disinfectant, the container providing a soak position (22) and a discharge position (26). The sterilizer unit also includes a discharge unit (14) for cooperation with the container, the discharge unit defines a compression compartment (28) in which the absorbent body can be held. The discharge unit is further movable between a release position in which the absorbent body can be located within the compression compartment and a compression position in which the discharge unit will apply a compressive force on the absorbent body inside the compression compartment. In use the compression compartment can be located within the soak position of the container when the discharge unit is located in its release position, thereby allowing the absorbent body to absorb an amount of disinfectant. The discharge unit can also be moved to its compression position when the compression compartment is located in the discharge position of the container, such that the absorbent body is allowed to dispense the disinfectant which it had absorbed when it was located inside the soak position of the container.

20 Claims, 7 Drawing Sheets

(56) References Cited

U.S. PATENT DOCUMENTS 7,892,485 B1 * 2/2011 Flannery et al. ............... 422/28
2004/0069810 A1   4/2004 Whitmore
2004/0191141 A1   9/2004 Margolis

OTHER PUBLICATIONS

International Search Report, Sep. 9, 2009, in counterpart foreign application under the WIPO, Application No. PCT/AU2009/000922.

* cited by examiner

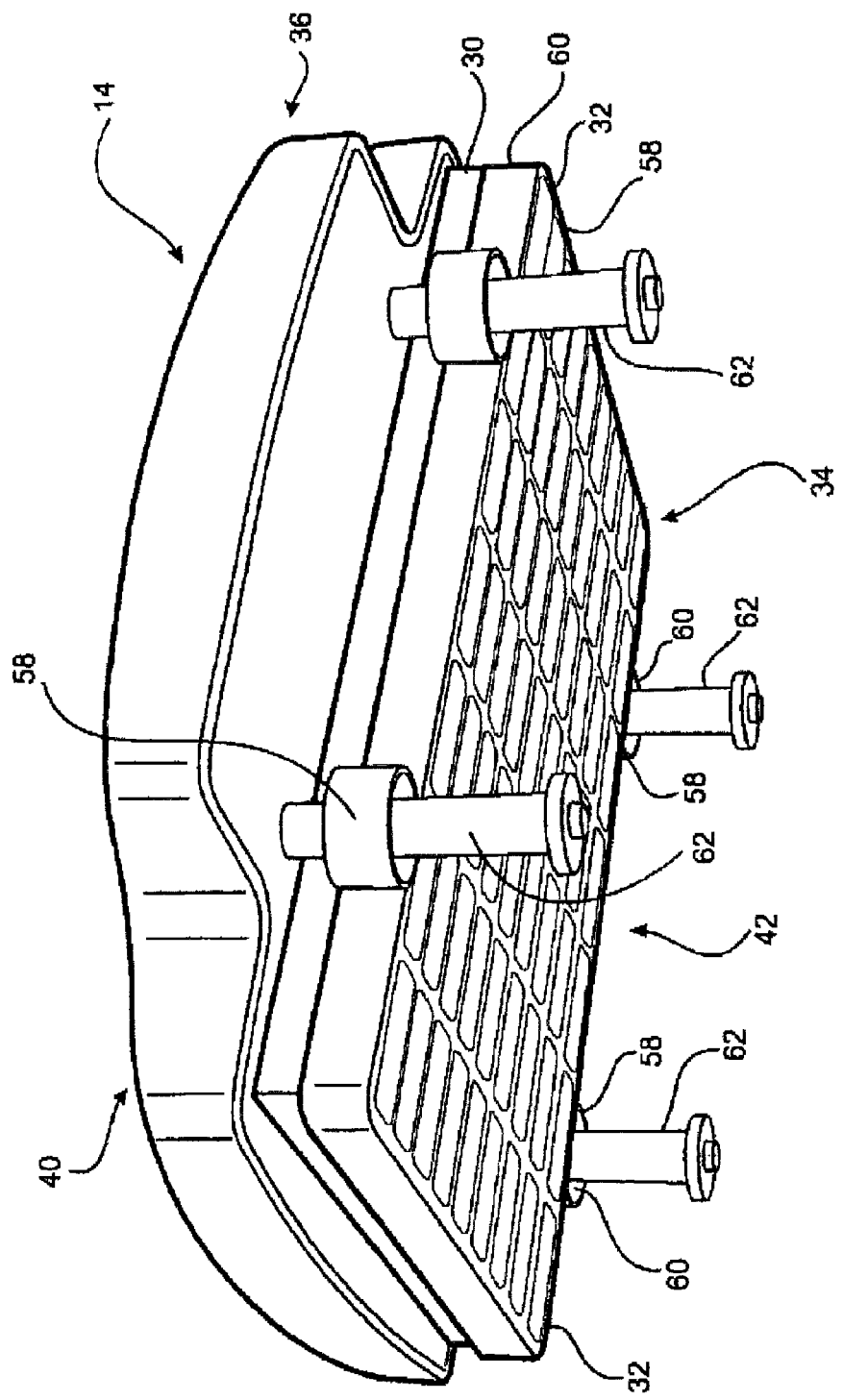

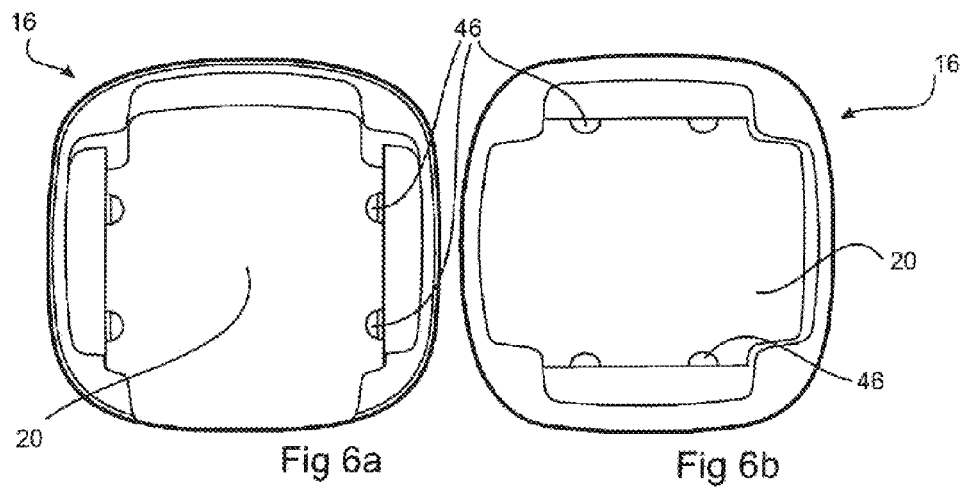
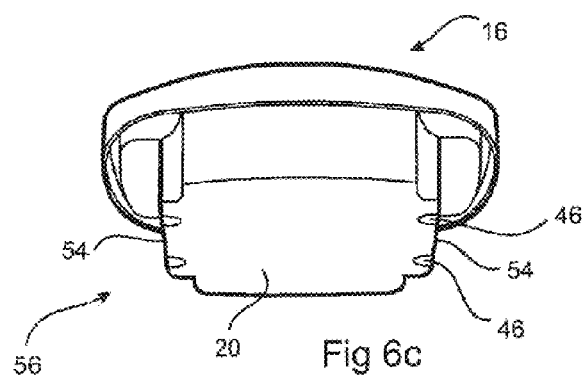
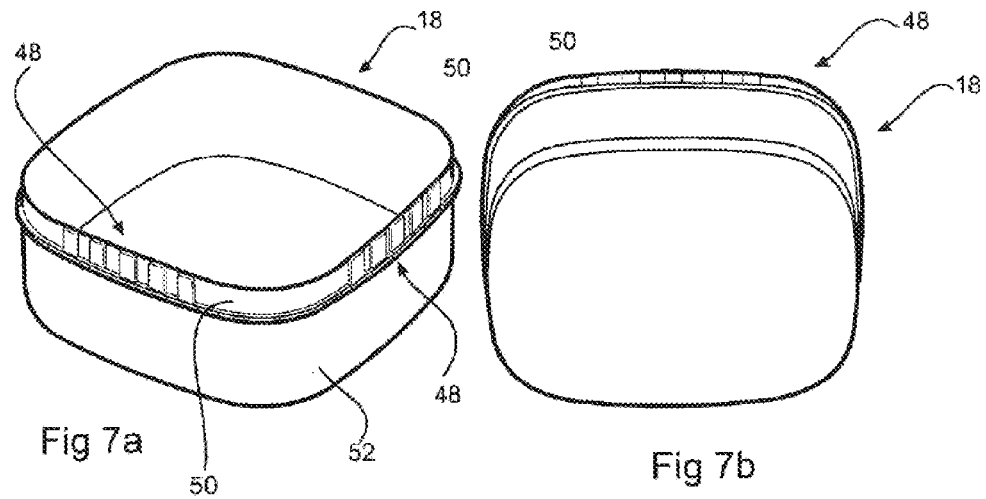

STERILISER UNIT

FIELD OF THE INVENTION

This invention relates to a steriliser unit. In particular the invention is concerned with a steriliser unit which can be used in sterilising an absorbent body, such as a sponge.

BACKGROUND ART

The following discussion of the background art is intended to facilitate an understanding of the present invention only. The discussion is not an acknowledgement or admission that any of the material referred to is or was part of the common general knowledge as at the priority date of the application.

Sponges are used in a range of applications for cleaning liquid impervious surfaces. Such applications include domestic cleaning of baths, basins, floors and table tops. Sponges are also used in a range of medical cleaning applications.

Typically sponges are produced from porous materials which display good liquid absorbing characteristics, particularly for absorbing water and water-based solutions. Materials employed in producing sponges generally include cellulose wood fibres and foamed plastic polymers. Although some natural sponges are still commercially available for use in cleaning applications, most natural sponges are used as body/facial sponges or as decorating tools for sponge painting. Synthetic sponges, on the other hand, are generally produced from low-density polyether, polyester and polyvinyl acetate (PVC).

A drawback associated with conventional sponges is that they can provide a favourable breeding ground for harmful bacteria or fungi. This is particularly true in the case where a sponge is allowed to remain wet between periods of use.

One manner in which bacteria infecting a sponge can be killed is by soaking the sponge in clean water and thereafter subjecting it to electromagnetic waves inside a conventional microwave oven. A disadvantage, however, in making use of this method of sterilising a sponge is that the sponge could be set alight if it was not properly soaked prior to being placed inside the microwave oven.

It is an object of the present invention to provide an alternative unit which can be used in sterilising an absorbent body, such as a sponge.

DISCLOSURE OF THE INVENTION

According to the present invention there is provided a steriliser unit for sterilising an absorbent body, such as a sponge, the steriliser unit comprising:
  a container for holding a disinfectant, the container providing a soak position and a discharge position; and
  a discharge unit for cooperation with the container, the discharge unit defining a compression compartment in which the absorbent body can be held, the discharge unit further being movable between a release position in which the absorbent body can be located within the compression compartment and a compression position in which the discharge unit will apply a compressive force on the absorbent body inside the compression compartment;
wherein the compression compartment can be located within the soak position of the container when the discharge unit is located in its release position, thereby allowing the absorbent body to absorb an amount of disinfectant, and further wherein the discharge unit can be moved to its compression position when the compression compartment is located in the discharge position of the container, such that the absorbent body is allowed to dispense the disinfectant which it had absorbed when it was located inside the soak position of the container.

Preferably the container includes a venting formation for in use allowing air, which is released by the absorbent body as it is caused to dispense its disinfectant, to vent to the atmosphere.

More preferably the container comprises an outer container body and an inner container body which are detachably connectable.

Advantageously the inner container body has a base which provides the soak position.

Advantageously the inner container body includes support edges which are raised above its base in order to provide the discharge position.

Typically the venting formation of the container is formed by a number of holes in the base of the inner container body and a number of protuberances located towards upper edges of the outer surface of the outer container body, and wherein outer surfaces of the inner container body define an outlet path for providing fluid communication between the holes in the base and the protuberances of the outer container body.

Preferably the discharge unit comprises a support member on which the absorbent body can be placed and a plunger which is movably connectable to the support member and wherein the compression compartment of the discharge unit is provided by an area between the support member and the plunger.

Preferably the plunger includes a number of legs.

Typically the support member includes a latticework structure having a number of lugs. Each lug in turn has a hole through which a leg of the plunger can slidably move.

Advantageously the discharge unit is configured to move from its release position to its compression position when the legs of the plunger are caused to slide through corresponding holes of the support member lugs.

Preferably the plunger comprises a first and a second plunger member which are detachably connectable.

More preferably the first plunger member includes a handle formation whereby a user can firstly cause the compression compartment to be moved between the soak position and the discharge position of the container and secondly cause the discharge unit to move between its release position and compression position.

Typically the legs are connected to the second plunger member and extend outwardly therefrom.

In an embodiment of the invention the legs of the plunger are provided with stops to prevent the lugs of the support member becoming separated from their corresponding plunger legs.

BRIEF DESCRIPTION OF THE DRAWINGS

The invention will now be described in more detail, by way of example only, with reference to the accompanying representations wherein:

FIG. 5 shows a bottom perspective view of the discharge unit located in its compression position and applying a compressive force on the absorbent body;

FIGS. 6(a), 6(b) and 6(c) respectively shown bottom, top and side perspective views of an inner container body of the container;

FIGS. 7(a) and 7(b) respectively show top and bottom perspective views of an outer container body of the container;

BEST MODE(S) FOR CARRYING OUT THE INVENTION

Throughout the specification and claims, unless the context requires otherwise, the word "comprise" or variations such as "comprises" or "comprising", will be understood to imply the inclusion of a stated integer or group of integers but not the exclusion of any other integer or group of integers.

Figure 1:
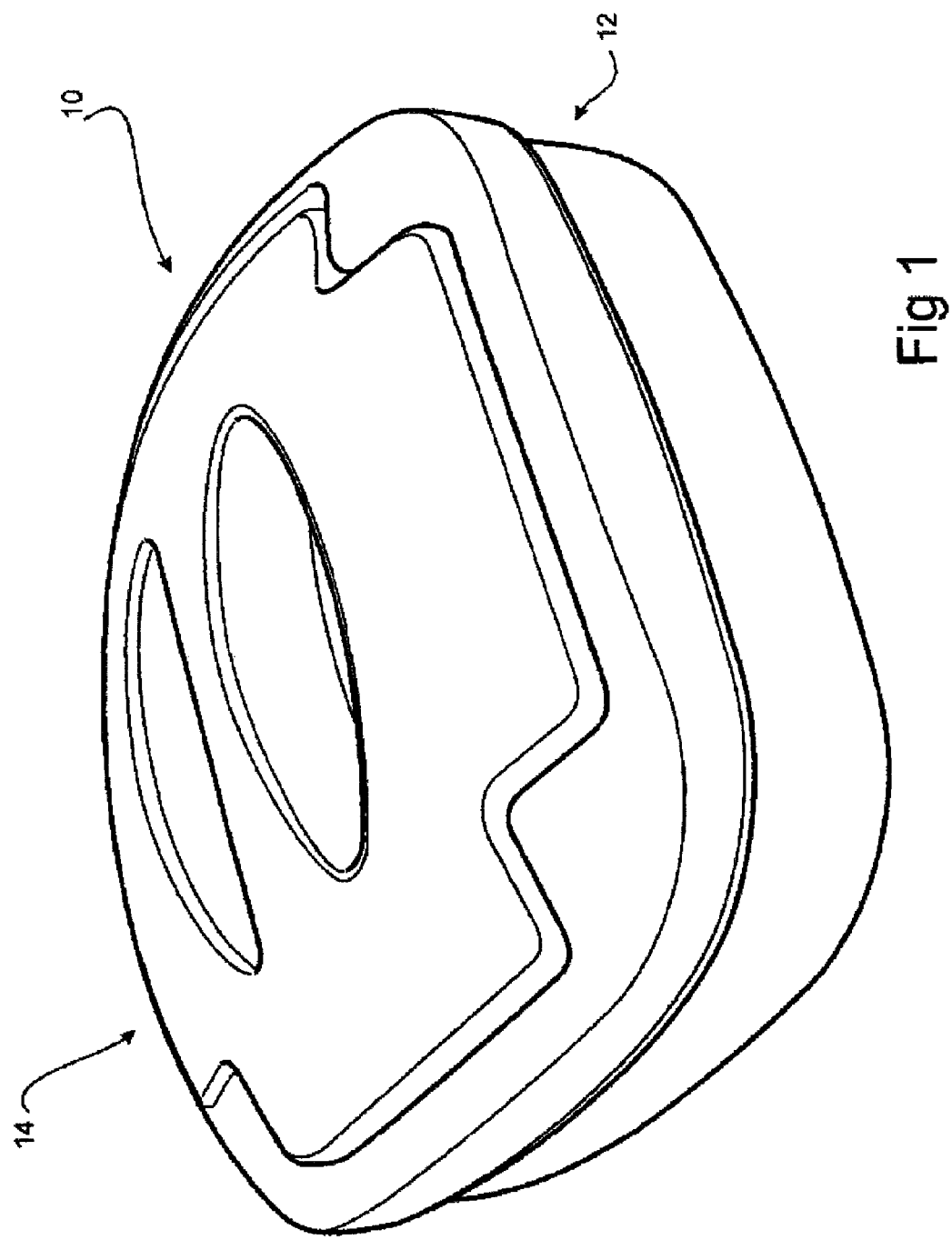
FIG. 1 shows a perspective view of a steriliser unit in accordance with the invention.

FIG. 1 shows a perspective view of a dispenser unit in accordance with the present invention, generally indicated with the reference numeral 10. The steriliser unit 10 comprises a container 12 which holds a discharge unit 14. The illustrated steriliser unit 10 is useful for sterilising an absorbent body, particularly an absorbent body in the form of a sponge, with the use of a liquid disinfectant held inside the container.

Figure 2:
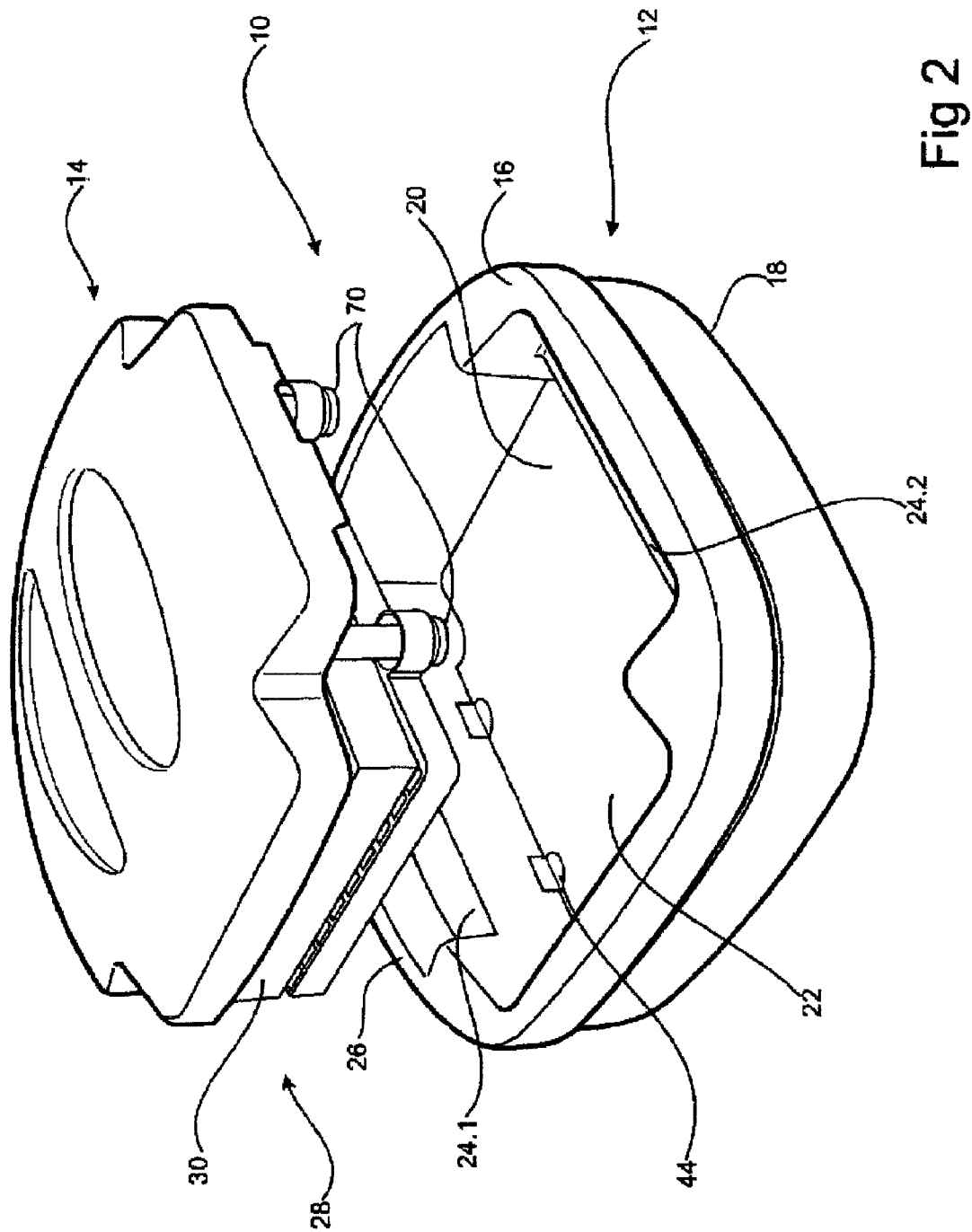
FIG. 2 shows a perspective view of the steriliser unit wherein an absorbent body held inside a compression compartment of a discharge unit of the steriliser unit, has been removed from a soak position of a container of the steriliser unit.

In FIG. 2 the discharge unit 14 is shown to have been removed from the container 12. It is pointed out that the container 12 comprises an inner container body and an outer container body, respectively indicated with the reference numerals 16 and 18, which are detachably connectable. The inner container body 16 includes a base 20 which is shaped as shown and provides a soak position 22 for the container 12. The inner container body 16 also includes support edges 24.1 and 24.2 which are raised above the base 20 in order to provide a discharge position 26 for the container 12. The purpose of the soak and discharge positions 22 and 26 will become apparent from the description which follows.

The discharge unit 14 defines a compression compartment 28 in which an absorbent body 30, here in the form of a sponge used for domestic cleaning purposes, is shown to be held. It is pointed out that the discharge unit 14 is orientated such that the compression compartment 28 together with the absorbent body 30 which it holds can be located inside the soak position 22 of the container 12, in use submerging the absorbent body 30 in liquid disinfectant and allowing it to absorb an amount of disinfectant.

Figure 3:
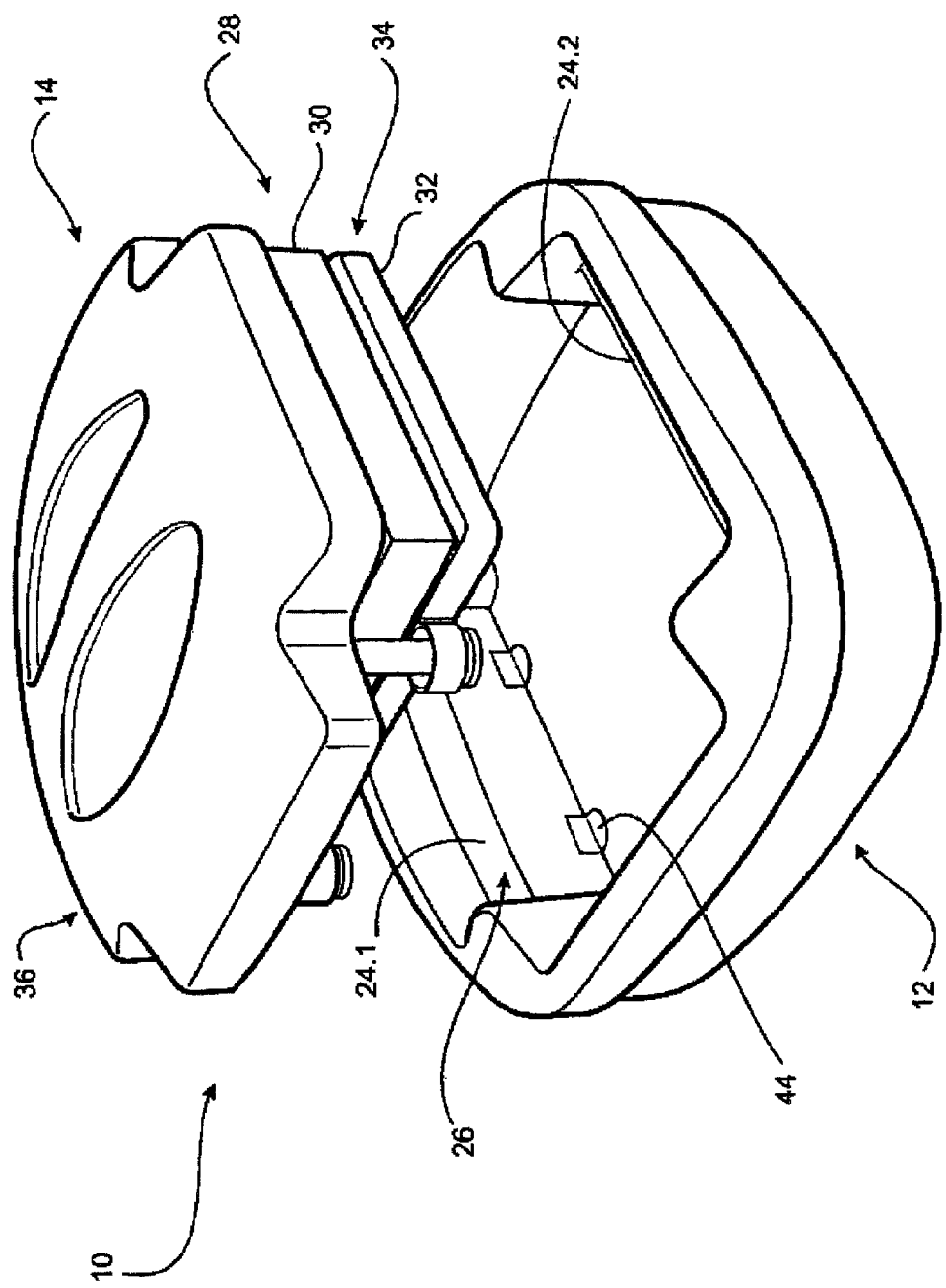
FIG. 3 shows a perspective view of the discharge unit wherein it has been orientated such that the compression compartment can be located in the discharge position of the container.

In FIG. 3 the discharge unit 14 has been orientated such that the compression compartment 28 can be located in the discharge position 26 of the container 12. When the discharge unit 14 is located in the discharge position 26 of the container 12, edge portions 32 of the discharge unit 14 will rest on the support edges 24.1 and 24.2 of the container 12. The discharge unit 14 of the illustrated embodiment comprises a support member 34 on which the absorbent body 30 can be placed. The discharge unit 14 also includes a plunger 36 which is movably connected to the support member 34 and wherein the compression compartment 28 is provided in the area between the support member 34 and the plunger 36.

Figure 4:
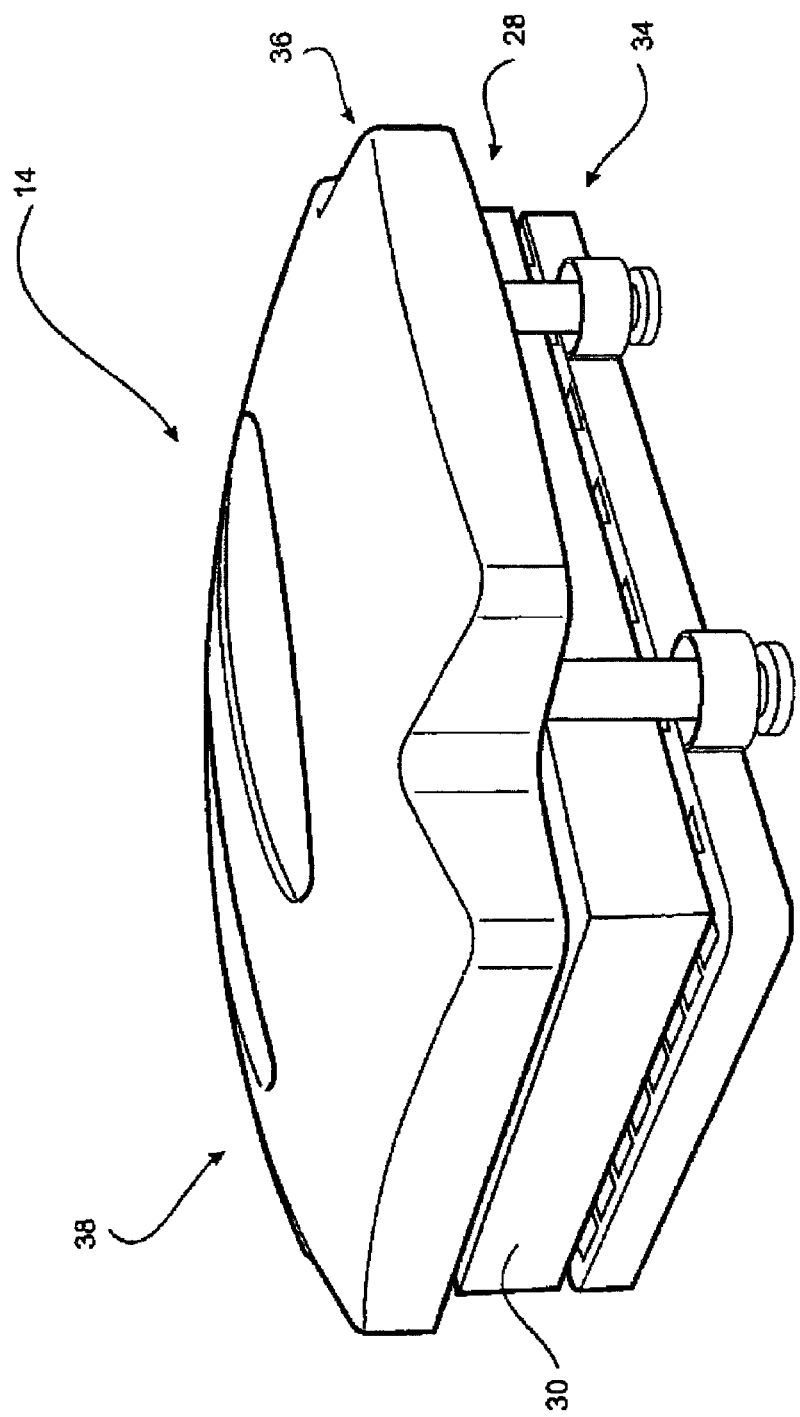
FIG. 4 shows a perspective view of the discharge unit located in its release position.
Figures 8A, 8B:
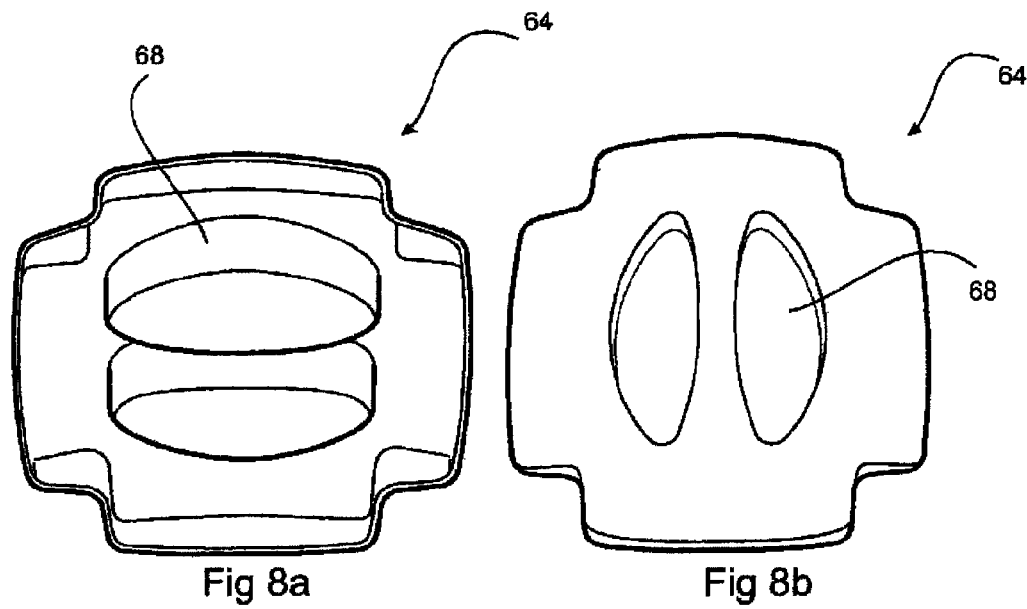
FIGS. 8(a) and 8(b) respectively show bottom and top perspective views of a first plunger member of the discharge unit.

The operation of the steriliser unit 10 will now be described with specific reference to FIG. 4 and FIG. 5 of the drawings. FIG. 4 shows the discharge unit 14 located in a release position 38 in which the support member 34 and the plunger 36 are spaced apart such that the absorbent body 30 can be located within the compression compartment 28. Typically the discharge unit 14, located in its release position 38, will be located in the soak position 20 of the container 12 when it is required to steriliser the absorbent body 30. With the discharge unit 14 located in its release position 38 inside the soak position 22 of the container 12, the absorbent body 30 will be allowed to absorb an amount of disinfectant liquid, thereby destroying fungi and bacteria which may inhabit the absorbent body 30.

When a user now requires use of the absorbent body 30 it will first be necessary to dispense the liquid disinfectant which had been absorbed thereby. The first step in dispensing the disinfectant will be to remove the discharge unit 14 from the container 12 and thereafter orientating it in the manner shown in FIG. 3, such that the edge portions 32 of the discharge unit 14 are aligned with the support edges 24.1 and 24.2 of the container 12. Hereafter the support member 34 is placed on the support edges 24.1 and 24.2, thereby locating the discharge unit 14 in its discharge position 26. The user can now apply a downward pressure on the discharge unit 14, thereby causing the plunger 36 to undergo movement relative to the support member 34. As the plunger 36 is caused to move relative to the support member 34 the dimensions of the compression compartment will be reduced, thus resulting in the discharge unit applying a compressive force to the absorbent body 30. As a result of the compressive force being applied thereon the absorbent body 30 will be caused to dispense the disinfectant which it had absorbed when it was located inside the soak position 22 of the container 12. In FIG. 5 the discharge unit 14 has been located in its compression position 40 where the plunger 36 has undergone its maximum movement relative to the support member 34 and the absorbent body 30 has undergone a sufficient amount of compression to dispense most of the disinfectant previously absorbed. The dispensed disinfectant will fall under the influence of gravity towards the base 20 of the container for future use. In this regard it is pointed out that the support member 34 includes a latticework structure 42 configured as shown to facilitate return of the dispensed disinfectant to the container 12. When it is again required to disinfect the absorbent body 30 the above procedure can simply be repeated.

FIGS. 6(a), 6(b) and 6(c) show the inner container body 16 removed from the outer container body 18. The outer container body 18 in turn is depicted in FIGS. 7(a) and 7(b). An important feature of the inner and outer container bodies 16 and 18 is that they cooperate with one another to provide that the container 12 includes a venting formation, generally indicated in with the reference numeral 44 in FIG. 2 and FIG. 3. The purpose of the venting formation 44 is to allow air which is released by the absorbent body when it is caused to dispense its disinfectant, to vent to the atmosphere.

In this exemplary embodiment of the invention the venting formation 44 is formed by firstly providing a number of holes 46 in the base 20 of the inner container body 16. The venting formation 44 also includes that a number of protuberances 48 be provided towards upper edges 50 of the outer surface 52 of the outer container body 18. Finally the outer surfaces 54 of the inner container body 16 define an outlet patch 56 for providing fluid communication between the holes 46 in the base 20 and the protuberances 48 of the outer container body 18.

Referring to FIG. 5 of the drawings it is pointed out that the latticework structure 42 of the support member 34 is provided with a number of lugs 58, in this embodiment there are four lugs, which are disposed about the perimeter of the support member as shown. Each lug 58, in turn, has a hole 60 through which a leg 62 of the plunger 36 can slidably move. In this regard it is pointed out that the discharge unit 14 will be caused to move from its release position 38, shown in FIG. 4, to its compression position 40 when the legs 62 of the plunger 36 are caused to slide through the their corresponding holes 60 of the support member lugs 58. This of course will occur in the event of a user applying a downward force on the discharge unit 14 as discussed above.

It is pointed out that the plunger 36 comprises first and second plunger members which are detachably connectable. The first and second plunger members are respectively shown in FIGS. 8(a) and 8(b) and FIGS. 9(a) and 9(b) and indicated with the reference numerals 64 and 66.

The first plunger member 64 includes a handle formation 68 which a user can grip when it is firstly required to cause the compression compartment 28 to be moved between the soak position 22 and the discharge position 26 of the container 12, shown in FIG. 2. Secondly, the user can grip the handle formation 68 when it is required to cause the discharge unit 14 to move between its release position 38, shown in FIG. 4, and its discharge position 26, shown in FIG. 5.

Figures 9A, 9B:
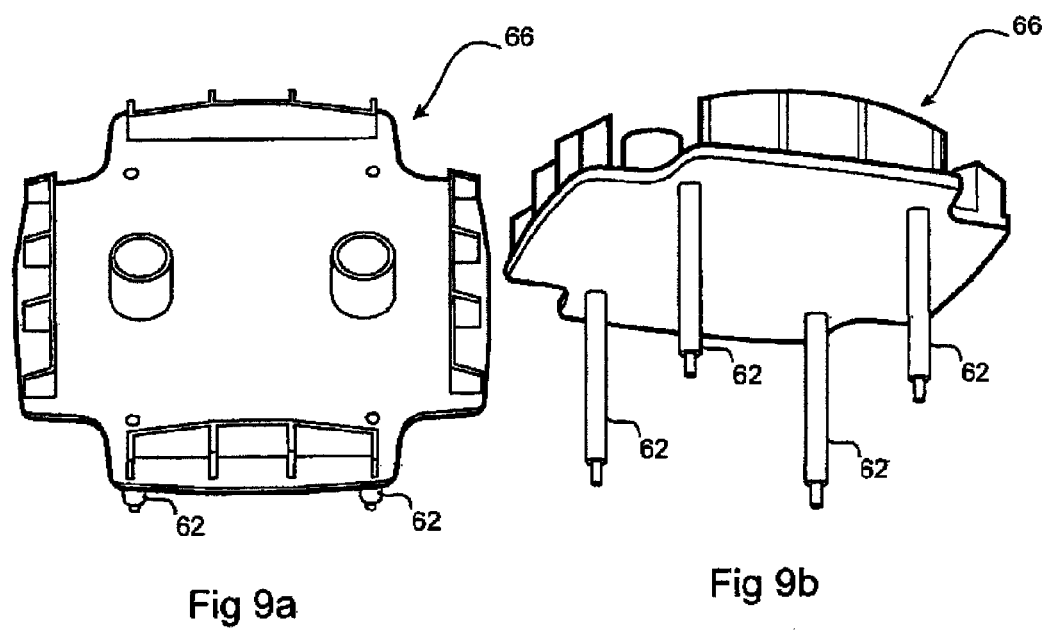
FIGS. 9(a) and 9(b) respectively show bottom and top perspective views of a second plunger member of the discharge unit.

Referring to FIGS. 9(a) and 9(b) it is pointed out that the legs 62 of the discharge unit 14 are connected to the second plunger member 66 and extend outwardly therefrom. In the illustrated embodiment the legs 62 of the plunger 36 will be provided with stops 70, shown in FIG. 2 of the drawings, to prevent the lugs 58 of the support member 34 becoming separated from their corresponding plunger legs 62.

It is envisaged that the steriliser unit of the invention will be produced from a plastics material, but it would be readily appreciated that a range of materials could be used in constructing a steriliser unit in accordance with the teaching of the present invention.

Although specific mention has been made to the use of the steriliser unit for sterilising a sponge, it would also be appreciated that the steriliser could be used for sterilising a range of absorbent articles.

A steriliser unit in accordance with the above description provides a useful apparatus which can be used to ensure that harmful bacteria and fungi which may inhibit an absorbent article, such as a sponge, are destroyed prior to being used for cleaning a specific surface.

The claims defining the invention are as follows:

1. A steriliser unit for sterilising an absorbent body comprising:
   a container comprising a reservoir having a base and a periphery surrounding the base for holding a disinfectant within the reservoir, the periphery being configured to provide a soak position and a discharge position; and
   a discharge unit for cooperation with the container, the discharge unit defining a compression compartment in which the absorbent body can be held, the discharge unit further being movable between a release position in which the absorbent body can be located within the compression compartment and a compression position in which the discharge unit will apply a compressive force on the absorbent body inside the compression compartment;
   wherein the periphery comprises a plurality of support surfaces arranged in a spaced apart relationship with respect to each other defining first and second accesses for the compression compartment to enter into the container, in the first access edges of the compression compartment are aligned with the support surfaces locating the discharge unit into the discharge position, and in the second access the edges of the compression compartment avoid alignment with the support surfaces locating the discharge unit into the soak position.

2. A steriliser unit according to claim 1 wherein the container includes a venting formation for in use allowing air, which is released by the absorbent body as the absorbent body is caused to dispense absorbed disinfectant, to vent to the atmosphere.

3. A steriliser unit according to claim 1, wherein the container comprises an outer container body and an inner container body which are detachably connectable.

4. A steriliser unit according to claim 3, wherein the inner container comprises the base and the periphery surrounding the base for holding a disinfectant within the reservoir.

5. A steriliser unit according to claim 4 wherein the inner container includes support edges defining the support surface, the support edges being raised above the base defining the support surface for mounting portions of the discharge unit to provide the discharge position.

6. A steriliser unit according to claim 1 wherein the discharge unit comprises a support member on which the absorbent body can be placed and a plunger which is movably connectable to the support member.

7. A steriliser unit according to claim 6 wherein the compression compartment of the discharge unit is provided by an area between the support member and the plunger.

8. A steriliser unit according to claim 6 wherein the plunger includes a number of legs.

9. A steriliser unit according to claim 8 wherein the support member includes a latticework structure having a number of lugs.

10. A steriliser unit according to claim 9 wherein each lug has a hole through which a leg of the plunger can slidably move.

11. A steriliser unit according to claim 9 wherein the discharge unit is configured to move from the release position to the compression position when the legs of the plunger are caused to slide through corresponding holes of the support member lugs.

12. A steriliser unit according to claim 6 wherein the plunger comprises a first and a second plunger member which are detachably connectable.

13. A steriliser unit according to claim 12 wherein the first plunger member includes a handle formation whereby a user can firstly cause the compression compartment to be moved between the soak position and the discharge position of the container and secondly cause the discharge unit to move between the release position and compression position.

14. A steriliser unit according to claim 12 wherein the legs are connected to the second plunger member and extend outwardly therefrom.

15. A steriliser unit according to claim 14 wherein the legs of the plunger are provided with stops to prevent the lugs of the support member becoming separated from their corresponding plunger legs.

16. A steriliser unit for sterilising an absorbent body comprising:
   a container for holding a disinfectant, the container providing a soak position and a discharge position; and
   a discharge unit for cooperation with the container, the discharge unit defining a compression compartment in which the absorbent body can be held, the discharge unit further being movable between a release position in which the absorbent body can be located within the compression compartment and a compression position in which the discharge unit will apply a compressive force on the absorbent body inside the compression compartment;

wherein the compression compartment is located within the soak position of the container when the discharge unit is located in the release position, thereby allowing the absorbent body to absorb an amount of disinfectant, and further wherein the discharge unit is adapted to be moved to the compression position when the compression compartment is located in the discharge position of the container, such that the absorbent body is allowed to dispense any disinfectant which the absorbent body absorbed while located inside the soak position of the container, wherein the container comprises an outer container and an inner container, the inner container comprising at least one inlet path for fluid communication between the inner container and the outer container.

17. A steriliser unit according to claim 16 wherein the outer container and the inner container are releasably attached to each other.

18. A steriliser unit according to claim 16 wherein the container includes a venting formation for in use allowing air, which is released by the absorbent body as the absorbent body is caused to dispense absorbed disinfectant, to vent to the atmosphere.

19. A steriliser unit according to claim 18 wherein the venting formation comprises the inlet path of the inner container body, and an outlet path for providing fluid communication between the inlet path and upper edges of the outer container body.

20. A steriliser unit according to claim 19, wherein the inlet path comprises a plurality of holes in the inner container and the outlet path comprises a plurality of protuberances located towards upper edges of the outer surface of the outer container body, and inner surface of the inner container body define a fluid path to allow allowing air, which is released by the absorbent body as it is caused to dispense its disinfectant, to vent to the atmosphere.

* * * * *